US005686386A

United States Patent [19]

Mabuchi et al.

[11] Patent Number: 5,686,386
[45] Date of Patent: Nov. 11, 1997

[54] HERBICIDAL COMPOSITION AND WEEDING METHOD

[75] Inventors: Tsutomu Mabuchi, Sakai; Motokatsu Nakatani, Kawachinagano; Takamichi Konno, Osakasayama, all of Japan

[73] Assignee: Nihon Nohyaku Co., Ltd., Tokyo, Japan

[21] Appl. No.: 574,630

[22] Filed: Dec. 19, 1995

Related U.S. Application Data

[63] Continuation of Ser. No. 141,082, Oct. 26, 1993, abandoned.

[30] Foreign Application Priority Data

Oct. 27, 1992 [JP] Japan ................... 4-311259

[51] Int. Cl.$^6$ ..................... A01N 43/56; A01N 57/00
[52] U.S. Cl. .......................... 504/128; 504/139
[58] Field of Search ..................... 504/128, 206, 504/139

[56] References Cited

U.S. PATENT DOCUMENTS

| | | | |
|---|---|---|---|
| 3,799,758 | 3/1974 | Franz | 504/206 |
| 3,977,860 | 8/1976 | Franz | 504/206 |
| 4,168,963 | 9/1979 | Rupp et al. | 504/201 |
| 4,309,208 | 1/1982 | Takematsu et al. | 504/190 |
| 4,315,765 | 2/1982 | Large | 504/206 |
| 4,448,601 | 5/1984 | Takematsu et al. | 504/117 |
| 4,455,163 | 6/1984 | Takematsu et al. | 504/117 |
| 4,552,584 | 11/1985 | Takematsu et al. | 504/117 |
| 4,622,060 | 11/1986 | Takematsu et al. | 504/117 |
| 4,659,860 | 4/1987 | Franz | 504/206 |
| 4,840,659 | 6/1989 | Franz | 504/206 |
| 5,032,165 | 7/1991 | Miura et al. | 546/14 |
| 5,112,384 | 5/1992 | Miura et al. | 548/366.1 |

FOREIGN PATENT DOCUMENTS

| | | |
|---|---|---|
| 0143547 | 6/1985 | European Pat. Off. . |
| 143547 | 6/1985 | European Pat. Off. . |
| 0232504 | 8/1987 | European Pat. Off. . |
| 0350880 | 1/1990 | European Pat. Off. . |
| 0361114 | 4/1990 | European Pat. Off. . |
| 3163063 | 7/1991 | Japan . |
| 3246204 | 11/1991 | Japan . |
| 459706 | 2/1992 | Japan . |

OTHER PUBLICATIONS

Chemical Patents Index, Documentation Abstracts Journal, Week 9215, 10 Jun. 1992 Derwent Pub. Ltd., AN 92-118314/15.

Chemical Patents Index, Documentation Abstracts Journal, Week 9150, 19 Feb. 1992, Derwent Pub. Ltd., AN 91-365755/50.

Streibig et al., "Herbicide Mixtures", Herbicide Bioassay, CRC Press (1993) pp. 120–129.

Zhang et al., "Antagonism and Synergism Between Herbicides: Trends From Previous Studies", Weed Technology (1995) 9:86–90.

Reviews of Weed Science, vol. 1, p. 35, 1985.

Chemical Patents Index, Documentation Abstracts Journal, Week 9215, 10 Jun. 1992, Derwent Publications Ltd., AN 92-118314/15 & JP-A-4 059 706 (Nihon Noyaku K.K.) 26 Feb. 1992.

Chemical Patents Index, Documentation Abstracts Journal, Week 9150, 19 Feb. 1992, Derwent Publications Ltd., AN 91-365775/50 & JP-A-3 246 204 (Nihon Noyaku K.K.) 1 Nov. 1991.

*Primary Examiner*—Richard L. Raymond
*Assistant Examiner*—Brian G. Bembenick
*Attorney, Agent, or Firm*—Cushman Darby & Cushman IP Group of Pillsbury Madison & Sutro LLP

[57] ABSTRACT

The present invention relates to a herbicidal composition containing as active ingredients at least one organophosphorus compound and 3-substituted phenylpyrazole derivative of the general formula (I):

[wherein R is $-Y^1R^3$, $-Y^2CH(R^4)CO-OR^5$, $-COOCH(R^4)CO-Y^1R^5$ or $-COOR^6$ ($R^3$, $R^4$, $R^5$, $R^6$, $Y^1$ and $Y^2$ are specified groups), $R^1$ is a lower alkyl group, $R^2$ is a hydrogen atom, a lower alkyl group or a lower haloalkyl group, $X^1$ and $X^2$, which may be the same or different, are halogen atoms, Y is $-O-$, $-S-$, $-SO-$ or $-SO_2-$, and n is zero or 1]; and a weeding method using said composition.

8 Claims, 2 Drawing Sheets

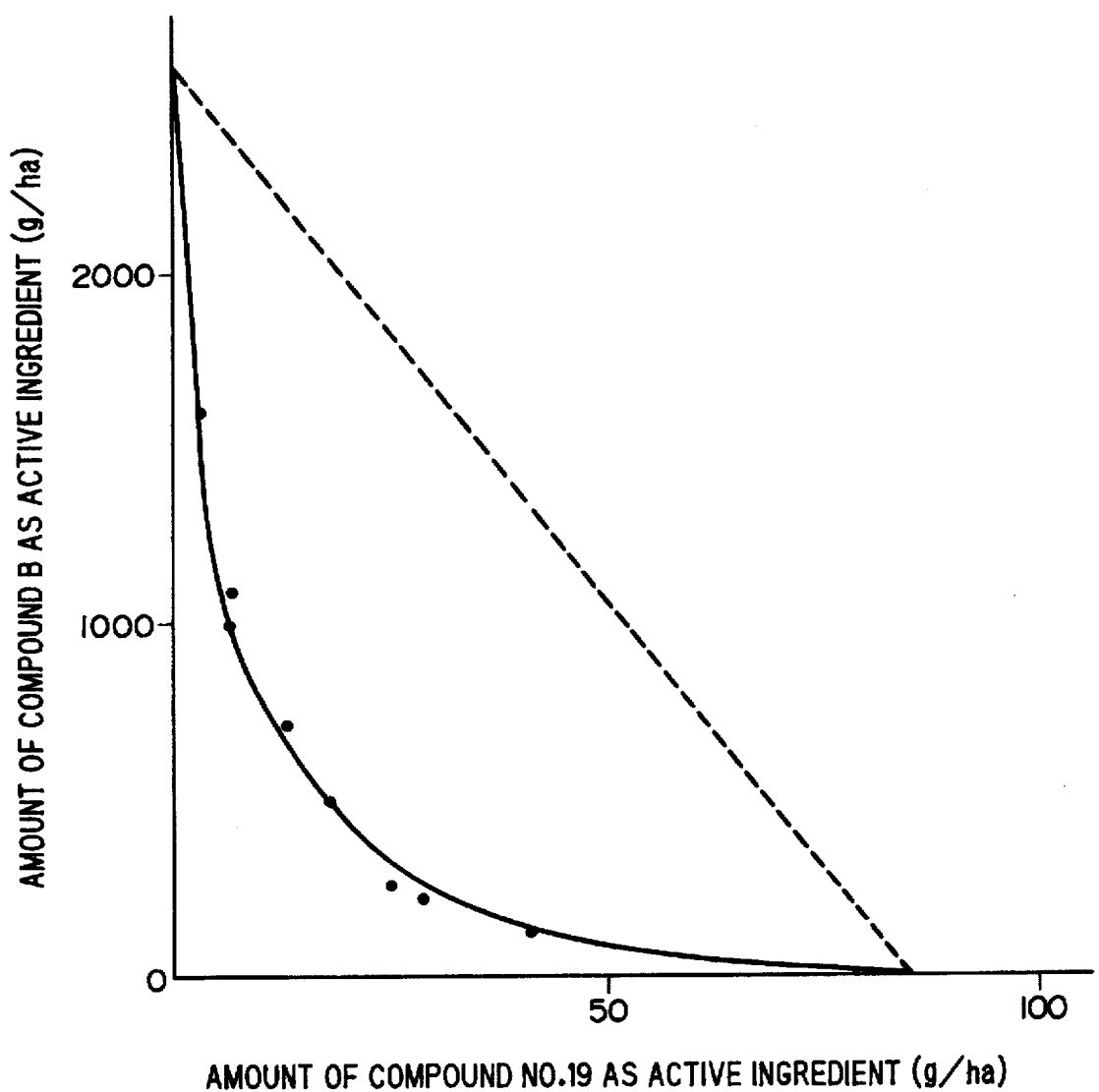

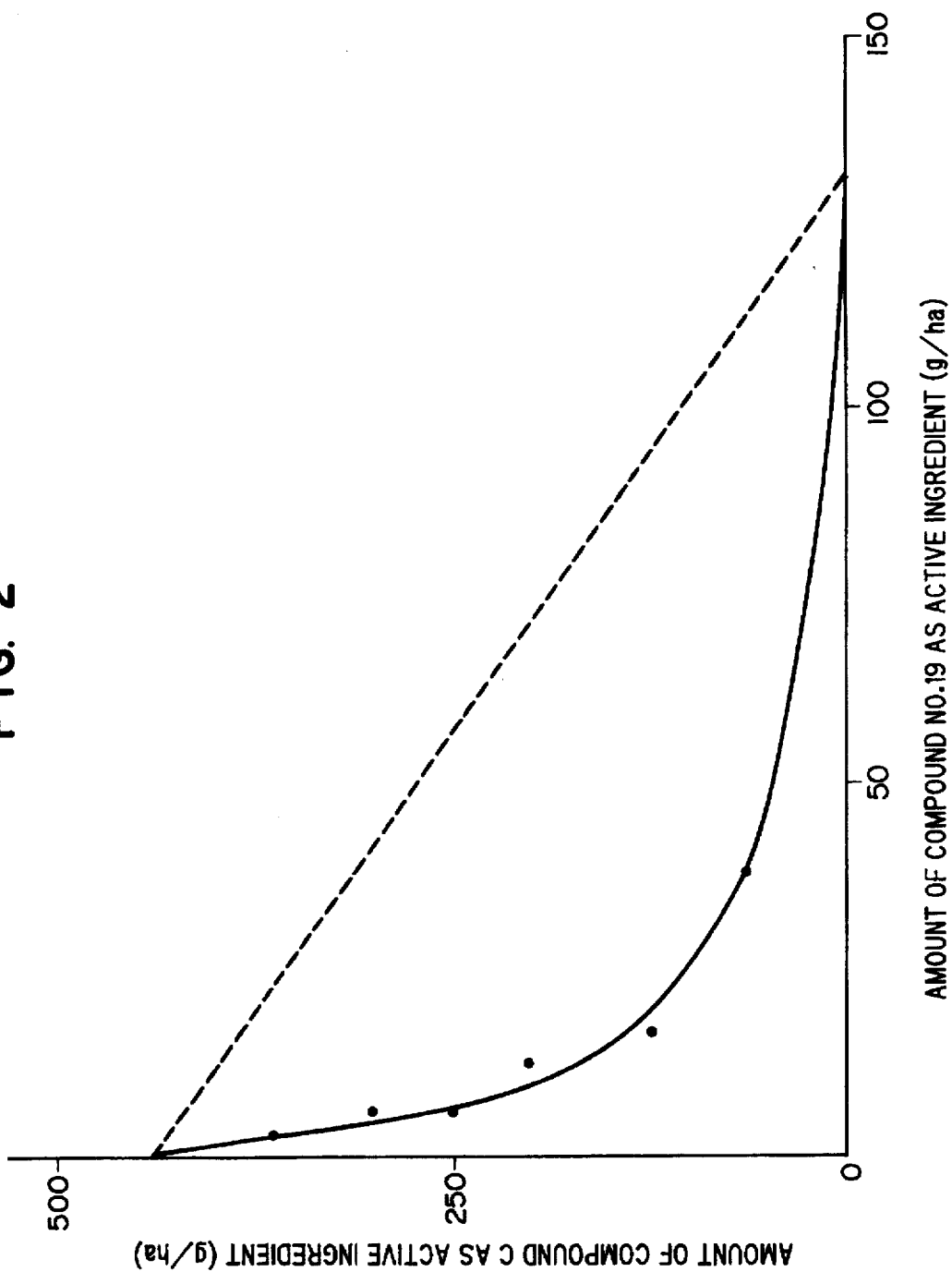

HERBICIDAL COMPOSITION AND WEEDING METHOD

This is a continuation of application Ser. No. 08/141,082, filed on Oct. 26, 1993, which was abandoned upon the filing hereof.

BACKGROUND OF THE INVENTION

1. Field of the Invention

This invention relates to a herbicidal composition containing as active ingredients at least one organophosphorous compound and a 3-substituted phenylpyrazole derivative represented by the general formula (I):

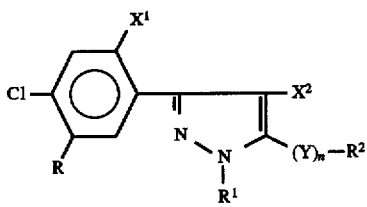

wherein R is

—$Y^1R^3$ (wherein $R^3$ is a lower alkyl group, a lower haloalkyl group, a lower alkenyl group or a lower alkynyl group, and $Y^1$ is —O— or —S—),

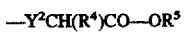

—$Y^2CH(R^4)CO$—$OR^5$ (wherein $R^4$ is a hydrogen atom or a lower alkyl group, $R^5$ is a hydrogen atom, a lower alkyl group, a lower haloalkyl group, a lower alkenyl group or a lower alkynyl group, and $Y^2$ is —O—, —S— or —NH—),

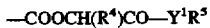

—COOCH($R^4$)CO—$Y^1R^5$ (wherein $R^4$, $R^5$ and $Y^1$ are as defined above), or

—$COOR^6$ (wherein $R^6$ is a lower alkyl group, a lower alkenyl group or a lower alkynyl group), $R^1$ is a lower alkyl group, $R^2$ is a hydrogen atom, a lower alkyl group or a lower haloalkyl group, $X^1$ and $X^2$, which may be the same or different, are halogen atoms, Y is —O—, —S—, —SO— or —$SO_2$—, and n is zero or 1; and a weeding method using said composition.

2. Related Art

The 3-substituted phenylpyrazole derivative of the general formula (I) is a compound described in Japanese Patent Unexamined Publication Nos. 3-163063 and 4-211065 and were found to be useful as a herbicide.

The organophosphorus compound used in the present invention is a well-known herbicide, for example, N-(phosphonomethyl)glycine or a salt thereof which are described in Japanese Patent Unexamined Publication Nos. 47-39538 and 57-95994, 4-[Hydroxy(methyl)phosphinoyl]-DL-homoalanine described in Japanese Patent Post-examined Publication No. 57-26564, or 4-[Hydroxy(methyl)-phosphinoyl]-L-homoalanyl-L-alanyl-L-alanine described in Japanese Patent Post-examined Publication No. 59-23282, etc.

Organophosphorus compounds are foliage applied herbicides widely used as non-selective herbicides, but they exhibit initial effect slowly and are not sufficiently effective against herbaceous weeds in developed leaf stage or reproduction stage. Therefore, there is an eager desire for the advent of a herbicide which exhibits herbicidal effect soon after application and has a sufficient herbicidal effect also on the herbaceous weeds in developed leaf stage or reproductive stage.

SUMMARY OF THE INVENTION

The present inventors earnestly investigated for solving such problems and consequently found that the simultaneous use of a 3-substituted phenylpyrazole derivative of the above general formula (I) and at least one organophosphorus compound gives fast-acting property and a wide weed control spectrum and moreover brings about an excellent synergistic effect at a dosage which is unexpectedly lower than a dosage required when each of the compounds is used alone, whereby the present invention has been accomplished.

BRIEF DESCRIPTION OF THE DRAWINGS

FIG. 1 is a graph showing the synergistic effect of a herbicidal composition (containing compound 19 and compound B) of the present invention by isobole analysis.

FIG. 2 is a graph showing the synergistic effect of a herbicidal composition (containing compound 19 and compound C) of the present invention by isobole analysis.

DETAILED DESCRIPTION OF PREFERRED EMBODIMENTS

The present invention relates to a herbicidal composition containing a compound of general formula (I) and at least one herbicidal organophosphorus compound as active ingredients, and a weeding method using said composition.

Examples of the compound of the general formula (I) are given in Table 1 but needless to say, they are not intended in any way to limit the scope of the present invention.

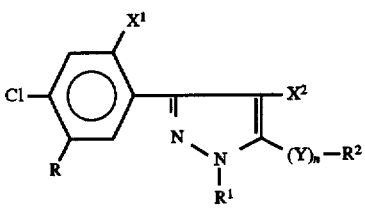

TABLE 1

(Examples of compound of the above general formula in which $R^1$ is $CH_3$ are given below.)

| No. | R | $R^2$ | $X^1$ | $X^2$ | $(Y)n$ | Physical properties |
|---|---|---|---|---|---|---|
| 1 | $OCH_2CH=CH_2$ | $CH_3$ | Cl | Cl | S | nD 1.6131 (25.3° C.) |
| 2 | $OCH_2CH=CH_2$ | $CHF_2$ | Cl | Cl | O | nD 1.5536 (28.4° C.) |
| 3 | $OCH_2CH=CH_2$ | $CHF_2$ | F | Cl | O | m.p. 63.7–64.1° C. |
| 4 | $SCH_2CH=CH_2$ | $CH_3$ | Cl | Cl | S | paste |
| 5 | $SCH_2CH=CH_2$ | $CHF_2$ | Cl | Cl | O | m.p. 52.0–55.0° C. |
| 6 | $SCH_2CH=CH_2$ | $CHF_2$ | F | Cl | O | nD 1.5670 (17.9° C.) |
| 7 | $OCH_2C\equiv CH$ | $CH_3$ | Cl | Cl | S | m.p. 71.5° C. |
| 8 | $OCH_2C\equiv CH$ | $CHF_2$ | Cl | Cl | O | m.p. 84.0° C. |
| 9 | $OCH_2C\equiv CH$ | $CHF_2$ | F | Cl | O | m.p. 98.0–98.1° C. |
| 10 | $SCH_2C\equiv CH$ | $CH_3$ | Cl | Cl | S | m.p. 94.5° C. |
| 11 | $SCH_2C\equiv CH$ | $CHF_2$ | Cl | Cl | O | m.p. 127–129° C. |
| 12 | $SCH_2C\equiv CH$ | $CHF_2$ | F | Cl | O | m.p. 82.8° C. |
| 13 | $OCH_2COOCH_3$ | $CH_3$ | Cl | Cl | S | m.p. 126.2° C. |
| 14 | $OCH_2COOCH_3$ | $CHF_2$ | Cl | Cl | O | m.p. 119.8° C. |
| 15 | $OCH_2COOCH_3$ | $CHF_2$ | Cl | Br | O | m.p. 133.8° C. |
| 16 | $OCH_2COOCH_3$ | $CHF_2$ | F | Cl | O | m.p. 122.8–123.1° C. |
| 17 | $OCH_2COOC_2H_5$ | $CH_3$ | Cl | Cl | S | m.p. 106.5° C. |
| 18 | $OCH_2COOC_2H_5$ | $CHF_2$ | Cl | Cl | O | m.p. 102.3° C. |
| 19 | $OCH_2COOC_2H_5$ | $CHF_2$ | F | Cl | O | m.p. 127.6° C. |
| 20 | $OCH_2COOC_3H_7$-n | $CHF_2$ | Cl | Cl | O | m.p. 89.7° C. |
| 21 | $OCH_2COOC_3H_7$-n | $CHF_2$ | F | Cl | O | m.p. 97.6–97.8° C. |
| 22 | $OCH_2COOC_3H_7$-i | $CHF_2$ | Cl | Cl | O | m.p. 106.0° C. |
| 23 | $OCH_2COOC_3H_7$-i | $CHF_2$ | F | Cl | O | m.p. 120.3–120.5° C. |
| 24 | $OCH_2COOCH_2CH=CH_2$ | $CHF_2$ | Cl | Cl | O | m.p. 84.7° C. |
| 25 | $OCH_2COOCH_2CH=CH_2$ | $CHF_2$ | F | Cl | O | m.p. 98.2–89.4° C. |
| 26 | $OCH_2COOCH_2C\equiv CH$ | $CHF_2$ | Cl | Cl | O | m.p. 119.6° C. |
| 27 | $OCH_2COOCH_2C\equiv CH$ | $CHF_2$ | F | Cl | O | m.p. 99.0° C. |
| 28 | $OCH(CH_3)COOH$ | $CH_3$ | Cl | Cl | S | m.p. 191–194° C. |
| 29 | $OCH(CH_3)COOCH_3$ | $CH_3$ | Cl | Cl | S | m.p. 90–93° C. |
| 30 | $OCH(CH_3)COOCH_3$ | $CHF_2$ | F | Cl | O | m.p. 95.6° C. |
| 31 | $OCH(CH_3)COOC_2H_5$ | $CH_3$ | Cl | Cl | S | nD 1.5763 (28.8° C.) |
| 32 | $OCH(CH_3)COOC_2H_5$ | $CHF_2$ | Cl | Cl | O | nD 1.5238 (25.7° C.) |
| 33 | $OCH(CH_3)COOC_2H_5$ | $CHF_2$ | Cl | Br | O | nD 1.5396 (20.8° C.) |
| 34 | $OCH(CH_3)COOC_2H_5$ | $CHF_2$ | F | Cl | O | m.p. 67.0–67.2° C. |
| 35 | $OCH(CH_3)COOC_3H_7$-i | $CH_3$ | Cl | Cl | S | m.p. 87–90° C. |
| 36 | $SCH(CH_3)COOCH_3$ | $CHF_2$ | Cl | Cl | O | nD 1.5654 (19.8° C.) |
| 37 | $SCH(CH_3)COOCH_3$ | $CHF_2$ | F | Cl | O | nD 1.5494 (25.0° C.) |
| 38 | $SCH(CH_3)COOC_2H_5$ | $CHF_2$ | Cl | Cl | O | nD 1.5565 (28.0° C.) |
| 39 | $SCH(CH_3)COOC_2H_5$ | $CHF_2$ | F | Cl | O | nD 1.5328 (18.0° C.) |
| 40 | $NHCH(CH_3)COOC_2H_5$ | $CH_3$ | Cl | Cl | S | m.p. 144.2° C. |
| 41 | $NHCH(CH_3)COOC_2H_5$ | $CH_3$ | Cl | Cl | S | paste |
| 42 | $NHCH(CH_3)COOC_2H_5$ | $CHF_2$ | Cl | Cl | O | nD 1.5371 (23.4° C.) |
| 43 | $NHCH(CH_3)COOC_2H_5$ | $CHF_2$ | F | Cl | O | nD 1.5264 (26.6° C.) |
| 44 | $COOCH_2COOCH_3$ | $CHF_2$ | Cl | Cl | O | m.p. 74.4° C. |
| 45 | $COOCH_2COOCH_3$ | $CHF_2$ | F | Cl | O | nD 1.5350 (27.3° C.) |
| 46 | $COOCH_2COSCH_3$ | $CHF_2$ | Cl | Cl | O | |
| 47 | $COOCH_2COSCH_3$ | $CHF_2$ | F | Cl | O | m.p. 57.2° C. |
| 48 | $COOCH_2COOC_2H_5$ | $CHF_2$ | Cl | Cl | O | m.p. 57.2° C. |
| 49 | $COOCH_2COOC_2H_5$ | $CHF_2$ | F | Cl | O | nD 1.5362 (23.4° C.) |
| 50 | $COOCH_2COSC_2H_5$ | $CHF_2$ | Cl | Cl | O | nD 1.5763 (20.7° C.) |
| 51 | $COOCH_2COSC_2H_5$ | $CHF_2$ | F | Cl | O | nD 1.5536 (27.3° C.) |
| 52 | $COOCH_2COOC_3H_7$-i | $CHF_2$ | Cl | Cl | O | nD 1.5289 (24.0° C.) |
| 53 | $COOCH_2COOC_3H_7$-i | $CHF_2$ | F | Cl | O | |
| 54 | $COOCH_2COOC_3H_7$-i | $CHF_2$ | Cl | Cl | O | nD 1.5684 (20.2° C.) |
| 55 | $COOCH_2COOC_3H_7$-i | $CHF_2$ | F | Cl | O | |
| 56 | $COOCH_2COOCH_2CH=CH_2$ | $CHF_2$ | Cl | Cl | O | m.p. 45.4° C. |
| 57 | $COOCH_2COOCH_2CH=CH_2$ | $CHF_2$ | F | Cl | O | |
| 58 | $COOCH_2COOCH_2C\equiv CH$ | $CHF_2$ | Cl | Cl | O | m.p. 79.3° C. |
| 59 | $COOCH_2COOCH_2C\equiv CH$ | $CHF_2$ | F | Cl | O | |
| 60 | $COOCH(CH_3)COOCH_3$ | $CHF_2$ | Cl | Cl | O | nD 1.5370 (25.7° C.) |
| 61 | $COOCH(CH_3)COOCH_3$ | $CHF_2$ | F | Cl | O | nD 1.5314 (23.0° C.) |
| 62 | $COOCH(CH_3)COOC_2H_5$ | $CHF_2$ | Cl | Cl | O | nD 1.5672 (26.0° C.) |
| 63 | $COOCH(CH_3)COOC_2H_5$ | $CHF_2$ | F | Cl | O | nD 1.5212 (14.1° C.) |
| 64 | $COOCH_2C\equiv CH$ | $CHF_2$ | Cl | Cl | O | m.p. 78.5° C. |
| 65 | $COOCH_3$ | $CHF_2$ | Cl | Cl | O | m.p. 63.9° C. |
| 66 | $COOCH_3$ | $CHF_2$ | F | Cl | O | nD 1.5430 (17.0° C.) |
| 67 | $COOC_2H_5$ | $CH_3$ | Cl | Cl | S | nD 1.6029 (20.1° C.) |
| 68 | $COOC_2H_5$ | $CHF_2$ | Cl | Cl | O | nD 1.5446 (26.8° C.) |
| 69 | $COOC_2H_5$ | $CHF_2$ | F | Cl | O | nD 1.5320 (21.0° C.) |
| 70 | $OCH_2CH=CH_2$ | $CHF_2$ | Cl | Cl | NH | m.p. 80.6° C. |
| 71 | $OCH_2C\equiv CH$ | $CHF_2$ | Cl | Cl | NH | m.p. 118.9° C. |
| 72 | $OCH_2COOCH_3$ | i-$C_3H_7$ | Cl | Cl | — | paste |
| 73 | $OCH_2CH=CH_2$ | i-$C_3H_7$ | Cl | Cl | — | paste |
| 74 | $OCH_2C\equiv CH$ | i-$C_3H_7$ | Cl | Cl | — | paste |

TABLE 1-continued (Examples of compound of the above general formula in which $R^1$ is $CH_3$ are given below.)

| No. | R | $R^2$ | $X^1$ | $X^2$ | $(Y)n$ | Physical properties |
|-----|---|-------|-------|-------|--------|---------------------|
| 75 | $SCH_2COOCH_3$ | $t-C_4H_9$ | Cl | Cl | — | paste |
| 76 | $OCH_2CH=CH_2$ | $CH_2Br$ | Cl | Cl | — | paste |

As the herbicidal organophosphorus compound, i.e., the other active ingredient used in the present invention, there can be used one or more compounds selected from the group consisting of N-(phosphonomethyl)glycine or a salt thereof, such as N-(phosphonomethyl)glycine isopropylammonium salt (hereinafter referred to as "compound A") or N-(phosphonomethyl)glycine trimethyl-sulfonium salt (hereinafter referred to as "compound B"); 4-[hydroxy (methyl)phosphinoyl]-DL-homoalanine or a salt thereof, such as 4-[hydroxy(methyl)phosphinoyl]-DL-homoalanine ammonium salt (hereinafter referred to as "compound C"); 4-[hydroxy(methyl)phosphinoyl]-L-homoalanyl-L-alanyl-L-alanine or a salt thereof, such as 4-[hydroxy(methyl) phosphinoyl]-L-homoalanyl-L-alanyl-L-alanine sodium salt (hereinafter referred to as "compound D"); etc. The organophosphorus compounds exemplified above are not intended in any way to limit the scope of the present invention.

For applying the herbicidal composition of the present invention, it may be prepared into suitable forms according to an ordinary manner for preparation of agrochemicals, depending on purposes. For example, said composition is blended with one or more materials selected from the group consisting of solid carriers, liquid carriers and surfactants, and optionally adjuvants, etc. and prepared into a preparation form such as water dispersible granules, a wettable powder, dust, a suspension concentrate, a soluble concentrate, or the like.

The active ingredients of the herbicidal composition of the present invention may be blended in optional proportions, depending on the type of formulation. The blending proportions of the active ingredients in said composition may be properly chosen in the following range: the proportion of organophosphorus compound is 0.01 to 1,000 parts by weight, preferably 1 to 500 parts by weight, per part by weight of 3-substituted phenylpyrazole derivative of the general formula (I).

The herbicidal composition of the present invention is useful as a non-selective herbicidal composition. The composition has fast-acting property which the organophosphorus compound does not have, by virtue of the simultaneous use of 3-substituted phenylpyrazole derivative and the organophosphorus compound, and moreover the composition permits reduction of the dosage because the simultaneous use brings about a synergistic effect which cannot be expected when each of the two agents is used alone.

The herbicidal composition of the present invention is useful particularly as a non-selective herbicide. The composition can be used, for example, for controlling weeds emerging in non-crop lands such as roads, building sites, railbeds, parks and playgrounds, and ground covering weeds in orchards, managed forests, forests, tame forests, etc. Furthermore, the composition can be used also as a weed management agent for levees of paddy fields and a clean up herbicide for fallow fields, and upland fields before planting. The composition is effective in controlling, for example, dicotyledons such as asiatic dayflower (*Commelina communis*), tufted knotweed (*Polygonum longisetum*), sweet scabious (*Erigeron annuus*), horseweed (*Erigeron canadensis*), shepherd's purse (*Capsella bursa-pastoris*), pale persicaria (*Polygonum lapathifolium*), livid amaranth (*Amaranthus lividus*), cudweed (*Gnaphalium affine*), three seeded copper leaf (*Acalypha australis*), slender amaranth (*Amaranthus varidis*), chickweed (*Stellaria media*), etc.; gramineous weeds such as large crabgrass (*Digitaria adscendens*), barnyard grass (*Echinochloa crus-galli*), annual bluegrass (*Poa annua*), water foxtail (*Alopecurus aequalis*), etc.; and perennial weeds such as curly dock (*Rumex juponicus*), mugwort (*Artemisia princeps*), field horsetail (*Equisetum arvense*), asiatic plantain (*Plantago asiatica*), philadelphia fleabane (*Erigeron philadelphicus*), dandelion (*Taraxacum officinale*), cogon grass (*Imperata cylindrica*), eulalia grass (*Miscanthus sinensis*), sorrel vine (*Cayratia japonica*), etc.

The present invention is applicable not only to the above places and weeds but also to all places and objective weeds for controlling undesirable weeds.

Although the herbicidal composition of the present invention is applied preferably during the early-post emergence or vegetative growth stage of weeds, its application time is not limited to these periods.

The dosage of the herbicidal composition of the present invention may be chosen in the range of 1 to 5,000 g (in terms of the active ingredients) per 10 ares.

When a compound such as 2-(4-isopropyl-4-methyl-5-oxo-2-imidazolin-2-yl)nicotinic acid (common name: imazapyr), methyl sulfanilylcarbamate (common name: asulam) or the like is used together with the 3-substituted phenylpyrazole derivative of the general formula (I) in place of the organophosphorus compound, i.e., one of the active ingredients used in the present invention, there can be obtained the same effect as that obtained by using the organophosphorus compound together with said derivative.

EXAMPLES

Typical examples of the present invention are described below but should not be construed as limiting the scope of the invention.

In the examples, parts are all by weight.

Example 1

| | |
|---|---|
| Compound 19 | 0.2 part |
| Compound C | 18.5 parts |
| Genapol LRD (mfd. by Hoechst AG) | 20.0 parts |
| Glauber's salt | 20.0 parts |
| Clay | 16.3 parts |
| Bentonite | 10.0 parts |
| Hydrated silicic acid | 10.0 parts |
| Calcium ligninsulfonate | 5.0 parts |
| Total | 100.0 parts |

Granular wettable powder was prepared by mixing the predetermined amounts of compound 19, compound C, Glauber's salt, clay, bentonite and hydrated silicic acid uniformly, placing the resulting mixed powder in a fluidized-bed granulator, and spraying the mixed powder with an aqueous solution containing the predetermined amounts of Genapol LRD and calcium ligninsulfonate, followed by granulation and drying.

Example 2

| | |
|---|---|
| Compound 19 | 0.2 part |
| Compound C | 18.5 parts |
| Pluronic L-64 (mfd. by Asahi Denka Co. Ltd.) | 5.0 parts |
| Sodium alkylbenzensulfonate | 2.0 parts |
| Methylnaphtalene | 10.0 parts |
| Water | 64.3 parts |
| Total | 100.0 parts |

An aqueous suspension concentrate was prepared by mixing the predetermined amounts of compound 19 and methylnaphthalene to obtain a solution, adding compound C, Pluronic L-64, Sodium alkylbenzensulfonate and water to the solution, and mixing them uniformly by means of a high-speed agitator.

Example 3

| | |
|---|---|
| Compound 19 | 0.2 part |
| Compound B | 38.0 parts |
| Pluronic L-64 (mfd. by Asahi Denka Co. Ltd.) | 5.0 parts |
| Sodium alkylbenzenesulfonate | 2.0 parts |
| Methylnaphtalene | 10.0 parts |
| Water | 44.8 parts |
| Total | 100.0 parts |

An aqueous suspension concentrate was prepared by mixing the predetermined amounts of compound 19 and methylnaphthalene to obtain a solution, adding compound B, Pluronic L-64, sodium alkylbenzenesulfonate and water to the solution, and mixing them uniformly by means of a high-speed agitator.

Example 4

| | |
|---|---|
| Compound 19 | 0.2 part |
| Compound C | 18.5 parts |
| Hitenol No. 8 (mfd. by Dai-ichi Kogyo Seiyaku Co., Ltd.) | 3.0 parts |
| Calcium ligninsulfonate | 3.0 parts |
| Carplex #80 (mfd. by Shionogi & Co., Ltd.) | 5.0 parts |
| Clay | 70.3 parts |
| Total | 100.0 parts |

A wettable powder was prepared by mixing uniformly and grinding the above ingredients.

Example 5

| | |
|---|---|
| Compound 19 | 0.2 part |
| Compound B | 38.0 parts |
| Hitenol No. 8 (mfd. by Dai-ichi Kogyo Seiyaku Co., Ltd.) | 3.0 parts |
| Calcium ligninsulfonate | 3.0 parts |
| Carplex #80 (mfd. by Shionogi & Co., Ltd.) | 5.0 parts |
| Clay | 50.8 parts |
| Total | 100.0 parts |

A wettable powder was prepared by mixing uniformly and grinding the above ingredients.

Test Example 1

Synergistic-effect test on compositions of the present invention

A pot with a diameter of 12 cm and a height of 11 cm was filled with upland soil (sandy loam) and seeded with barnyard grass (*Echinochloa crus-galli*) so as to adjust the depth of covering soil to 0.5 cm, and the barnyard grass was grown in a greenhouse.

When the barnyard grass was grown to a leaf stage of 3 and a height of 10 cm in a test co-using compound B or a leaf stage of 5 and a height of 15 cm in a test co-using compound C, a predetermined amount of each herbicidal composition of the present invention was diluted with water and the dilution was sprayed from above uniformly on the whole surfaces of the stem and leaves in a spray volume of 1,000 liters per hectare by the use of a small-sized sprayer.

On the 10th day after the spraying, the degree of growth of the above-ground part of surviving barnyard grass plants was visually judged in the range of zero (ineffective) to 100 (complete kill) by comparison with that on the untreated plot.

The test results obtained in the composition of compound 19 and B or compound 19 and C are shown in Table 2 and Table 3, respectively.

TABLE 2

| | Amount of compound 19 as active ingredient (g/ha) | | | | | | |
|---|---|---|---|---|---|---|---|
| | 0 | 3.125 | 6.25 | 12.5 | 25.0 | 50.0 | 100.0 |
| Amount of compound B as active ingredient (g/ha) | | | | | | | |
| 0 | 0 | 30 | 50 | 50 | 80 | 85 | 90 |
| 125 | 40 | 40 | 50 | 60 | 85 | 95 | |
| 250 | 50 | 60 | 60 | 70 | 90 | 98 | |
| 500 | 60 | 70 | 70 | 80 | 95 | 99 | |
| 1000 | 70 | 80 | 90 | 95 | 98 | 100 | |
| 2000 | 90 | 95 | 98 | 99 | 100 | 100 | |

TABLE 3

| | Amount of compound 19 as active ingredient (g/ha) | | | | | | |
|---|---|---|---|---|---|---|---|
| | 0 | 3.125 | 6.25 | 12.5 | 25.0 | 50.0 | 100.0 |
| Amount of compound C as | | | | | | | |
| 0 | 0 | 40 | 50 | 60 | 70 | 80 | 90 |
| 62.5 | 50 | 50 | 60 | 60 | 90 | 95 | |
| 125 | 60 | 70 | 70 | 85 | 95 | 98 | |
| 250 | 80 | 85 | 90 | 95 | 98 | 99 | |

TABLE 3-continued

| | Amount of compound 19 as active ingredient (g/ha) | | | | | | |
|---|---|---|---|---|---|---|---|
| | 0 | 3.125 | 6.25 | 12.5 | 25.0 | 50.0 | 100.0 |
| active ingredient (g/ha) | 500 | 90 | 95 | 95 | 98 | 99 | 100 |
| | 1000 | 98 | 98 | 98 | 98 | 100 | 100 |

The above results are shown in the drawings for facilitating the understanding.

FIG. 1 shows a constant-effect curve drawn on the basis of the herbicidal effect on barnyard grass shown in Table 2 in the test example.

The axis of abscissa refers to the amount (g/ha) of compound 19 as active ingredient and the axis of ordinate to the amount (g/ha) of compound B as active ingredient.

The expected ED 90 isobole of additive effect is shown in the broken line and ED 90 isobole of the combination between compound 19 and compound B obtained in practice is shown in the solid line.

Similarly, the synergistic effect of the herbicidal composition (containing compound 19 and compound C) of the present invention is shown in FIG. 2.

As shown in FIG. 1 and FIG. 2, the herbicidal compositions of the present invention have synergistic effect clearly.

What is claimed is:

1. A herbicidal composition comprising as active ingredients a synergistic effective amount of at least one organophosphorous compound and a synergistic effective amount of a 3-substituted phenylpyrazole derivative represented by the general formula (I):

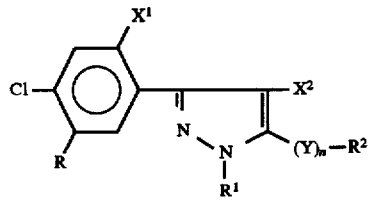

wherein R is

—Y$^1$R$^3$ (wherein R$^3$ is a lower alkyl group, a lower haloalkyl group, a lower alkenyl group or a lower alkynyl group, and Y$^1$ is —O— or —S—),

—Y$^2$CH(R$^4$)CO—OR$^5$ (wherein R$^4$ is a hydrogen atom or a lower alkyl group, R$^5$ is a hydrogen atom, a lower alkyl group, a lower haloalkyl group, a lower alkenyl group or a lower alkynyl group, and Y$^2$ is —O—, —S— or —NH—),

—COOCH(R$^4$)CO—Y$^1$R$^5$ (wherein R$^4$, R$^5$ and Y$^1$ are as defined above), or

—COOR$^6$ (wherein R$^6$ is a lower alkyl group, a lower alkenyl group or a lower alkynyl group), R$^1$ is a lower alkyl group, R$^2$ is a hydrogen atom, a lower alkyl group or a lower haloalkyl group, X$^1$ and X$^2$, which may be the same or different, are halogen atoms, Y is —O—, —S—, —SO— or —SO$_2$—, and n is zero or 1.

2. A herbicidal composition according to claim 1, wherein the organophosphorus compound is selected from the group consisting of N-(phosphonomethyl)glycine or a salt thereof, 4-[hydroxy (methyl)phosphinoyl]-DL-homoalanine or a salt thereof, 4-[hydroxy(methyl)phosphinoyl]-L-homoalanyl-L-alanyl-L-alanine or a salt thereof.

3. A herbicidal composition according to claim 2, wherein the organophosphorus compound is contained in an amount of 0.01 to 1,000 parts by weight per part by weight of the 3-substituted phenylpyrazole derivative of the general formula (I).

4. A herbicidal composition according to claim 3, wherein the herbicidal composition is a non-selective herbicide.

5. A method for controlling weeds which comprises applying a herbicidal composition in a dosage chosen in the range of 1 g to 5 kg (in terms of the active ingredients of the composition) per 10 ares for controlling undesirable weeds, said herbicidal composition comprising as active ingredients a synergistic effective amount of at least one organophosphorous compound and a synergistic effective amount of a 3-substituted phenylpyrazole derivative represented by the general formula (I):

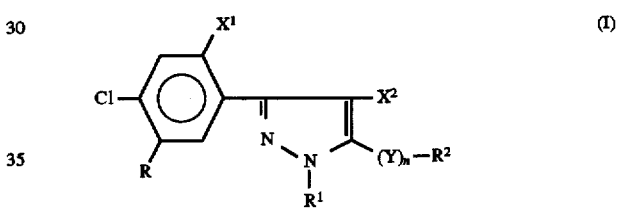

wherein R is

Y$^1$R$^3$ (wherein R$^3$ is a lower alkyl group, a lower haloalkyl group, a lower alkenyl group or a lower alkynyl group, and Y$^1$ is —O— or —S—),

—Y$^2$CH(R$^4$)CO—OR$^5$ (wherein R$^4$ is a hydrogen atom or a lower alkyl group, R$^5$ is a hydrogen atom, a lower alkyl group, a lower haloalkyl group, a lower alkenyl group or a lower alkynyl group, and Y$^2$ is —O—, —S— or —NH—),

—COOCH(R$^4$)CO—Y$^1$R$^5$ (wherein R$^4$, R$^5$ and Y$^1$ are as defined above), or

—COOR$^6$ (wherein R$^6$ is a lower alkyl group, a lower alkenyl group or a lower alkynyl group), R$^1$ is a lower alkyl group, R$^2$ is a hydrogen atom, a lower alkyl group or a lower haloalkyl group, X$^1$ and X$^2$, which may be the same or different, are halogen atoms, Y is —O—, —S—, —SO— or —SO$_2$—, and n is zero or 1.

6. A method for controlling weeds according to claim 5, wherein the organophosphorus compound is selected from the group consisting of N-(phosphonomethyl)glycine or a salt thereof, 4-[hydroxy(methyl)phosphinoyl]-DL-homoalanine or a salt thereof, 4-[hydroxy(methyl) phosphinoyl]-L-homoalanyl-L-alanyl-L-alanine or a salt thereof.

7. A herbicidal composition according to claim 2, wherein the organophosphorus compound is contained in an amount of 1 to 500 parts by weight per part by weight of the 3-substituted phenylpyrazole derivative of the general formula (I).

8. A method for controlling weeds which comprises the steps of applying a herbicidal composition in a dosage chosen in the range of 1 g to 5 kg, in terms of the active ingredients of the composition, per 10 ares for controlling undesirable weeds, said herbicidal composition comprising as active ingredients at least one herbicidal organophosphorus compound at a dosage insufficient to control weeds as a sole active ingredient and a synergistic effective amount of a 3-substituted phenylpyrazole derivative represented by the formula (I):

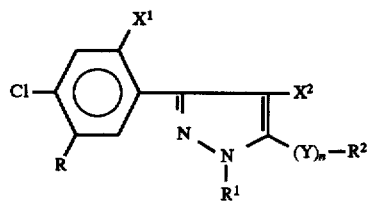
(I)

wherein R is

—$Y^1R^3$ wherein $R^3$ is a lower alkyl group, a lower haloalkyl group, a lower alkenyl group or a lower alkynyl group, and $Y^1$ is —O— or —S—,

—$Y^2CH(R^4)CO—OR^5$ wherein $R^4$ is a hydrogen atom, or a lower alkyl group, $R^5$ is a hydrogen atom, a lower alkyl group, a lower haloalkyl group, a lower alkenyl group or a lower alkynyl group, and $Y^2$ is —O—, —S— or —NH—,

—$COOCH(R^4)CO—Y^1R^5$ wherein $R^4$, $R^5$, and $Y^1$ are as defined above, or

—$COOR^6$ wherein $R^6$ is a lower alkyl group, a lower alkenyl group or a lower alkynyl group, $R^1$ is a lower alkyl group, $R^2$ is a hydrogen atom, a lower alkyl group or a lower haloalkyl group, $X^1$ and $X^2$, which may be the same or different, are halogen atoms, Y is —O—, —S—, —SO— or —SO$_2$—, and n is zero or 1.

* * * * *

UNITED STATES PATENT AND TRADEMARK OFFICE
CERTIFICATE OF CORRECTION

PATENT NO. : 5,686,386
DATED : November 11, 1997
INVENTOR(S) : MABUCHI, et al

It is certified that error appears in the above-identified patent and that said Letters Patent is hereby corrected as shown below:

Claim 1, line 11, change "-$Y^2CH(R^4)CO=OR^5$" to --$Y^2CH(R^4)CO\text{-}OR^5$--.

Signed and Sealed this

Fifth Day of January, 1999

Attest:

Attesting Officer

*Acting Commissioner of Patents and Trademarks*